United States Patent [19]

Goldberg et al.

[11] Patent Number: 4,984,574

[45] Date of Patent: Jan. 15, 1991

[54] NONINVASIVE FETAL OXYGEN MONITOR USING NMR

[76] Inventors: Seth Goldberg, 630 First Avenue (Apt. 14J), New York, N.Y. 10016; Jonothan L. Logan, Birch Hill Rd., R.D. 1, Box 2480, Westford, Vt. 05494

[21] Appl. No.: 275,447

[22] Filed: Nov. 23, 1988

[51] Int. Cl.$^5$ .............................................. A61B 5/055
[52] U.S. Cl. .................................. 128/653 A; 324/307
[58] Field of Search .................... 128/653 A; 324/307, 324/309; 436/173

[56] References Cited

U.S. PATENT DOCUMENTS

| | | | |
|---|---|---|---|
| 4,240,439 | 12/1980 | Abe et al. | 128/653 |
| 4,411,270 | 10/1983 | Damadien | 128/653 |
| 4,477,777 | 10/1984 | Gordon | 324/300 |
| 4,543,959 | 10/1985 | Sepponen | 128/653 |
| 4,564,017 | 1/1986 | Glover | 128/653 |
| 4,586,511 | 5/1986 | Clark, Jr. | 128/653 |
| 4,682,112 | 7/1987 | Beer | 324/322 |
| 4,694,837 | 9/1987 | Blakeley et al. | 128/653 |
| 4,721,914 | 1/1988 | Fukishima et al. | 128/653 |
| 4,734,039 | 3/1988 | Thompson | 434/273 |
| 4,770,182 | 9/1988 | Damadien et al. | 128/653 |

OTHER PUBLICATIONS

Smith et al., "Triplanar Proton Imaging in Pregnancy", MR in Medicine, vol. 1, No. 2, Jun. 1984, Academic Press, Inc., Article No. 195, pp. 259–260.

West–Jordan et al., "$^{31}$P NMR Studies on Recovery from Hypoxia of Human Tumor Cells", MR in Medicine, vol. 5, No. 2, Aug. 1987, Academic Press, Inc., pp. 182–185.

Reglinski et al., "Spin Echo 'H NMR Detected Response of Engothioneine to Oxidative Stress in the Intact Human Erythrocyte", MR in Medicine, vol. 6, No. 2, Feb. 1988, Academic Press, Inc., pp. 217–223.

Comstock et al., "Evaluation of Placenta Architecture with NMR Imaging Techniques", Magnetic Resonance in Medicine, vol. 1, No. 2, Jun. 1984, Academic Press, Inc., Article No. 53, pp. 136–137.

O'Donnell et al., "NMR Imaging Using a 0.15 T Resistive Magnet in a Magnetically Shielded Room", MR in Medicine, vol. 1, No. 2, Jun. 1984, Academic Press, Inc., Article No. 150, pp. 219.

Eidelberg et al., "$^{19}$F NMR Imaging of Blood Oxygenation in the Brain", MR in Medicine, vol. 6, No. 3, Mar. 1988, Academic Press, Inc., pp. 344–352.

D. G. Davis et al., "Nuclear Magnetic Resonance Studies of Hemoglobins. V. The Heme Proton Spectra of Human Deoxyhemoglobins A, F, Zürich, and Chesapeak". Biochemical and Biophysical Research Communications 40, 343–349 (1970).

(List continued on next page.)

Primary Examiner—Ruth S. Smith
Assistant Examiner—K. M. Pfaffle
Attorney, Agent, or Firm—Sprung, Horn, Kramer & Woods

[57] ABSTRACT

A non-invasive method for continuously monitoring blood and tissue oxygenation of a human fetus prior to and during labor and delivery. A specialized NMR spectrometer, whose static-field magnet is large enough to admit the abdomen of a pregnant woman at term, obtains resonance signals from a spatial region within the mother that includes the fetus. Resonance signals originating from the oxygen-transport protein hemoglobin are continuously obtained and analyzed. Signals originating from the special form of hemoglobin found in the fetal circulation are distinguished from those from the adult form of hemoglobin found in the maternal circulation. By continuously comparing the amplitudes of specific fetal hemoglobin resonances that are characteristically shifted upon oxygen binding with the amplitudes of other fetal hemoglobin resonances that are not so shifted, the method yields a continuous measurement of fetal blood and tissue oxygenation. Further analysis of the resonance signals yields indications of fetal blood acidity, heartbeat and respiration and corresponding indications of maternal condition. The method is also applicable to newborn infants and to certain mammals other than humans.

8 Claims, 4 Drawing Sheets

OTHER PUBLICATIONS

C. Ho et al., "Proton Nuclear Magnetic Resonance Investigation of Hemoglobins". Methods in Enzymology 76, 275–312 (Academic Press, NY, 1981).

C. Ho et al., "Nuclear Magnetic Resonance Studies of Hemoglobin. IV. Biochemical and Biophysical Research Communications", 779–785 (1970).

T. R. Lindstrom et al., "Nuclear Magnetic Resonance Studies of Hemoglobins, VII. Tertiary Structure Around Ligand Binding Site in Carbonmonoxyhemoglobin." Biochemistry 11, 1677–1681 (1972).

T. R. Lindstrom and C. Ho, "Effects of Anions and Ligands on the Tertiary Structure Around Ligand Binding Site in Human Adult Hemoglobin." Biochemistry 12, 134–139 (1973).

NONINVASIVE FETAL OXYGEN MONITOR USING NMR

FIELD OF THE INVENTION

The field of this invention is medical measurement and testing. Specifically, the invention relates to devices and methods for monitoring the physiological condition of human fetuses and newborns, especially during labor and delivery, for signs of distress.

BACKGROUND OF THE INVENTION

Fetal oxygen deprivation (hypoxia) is a significant cause of human fetal death and of damage to the brain and other organs of surviving infants. For this reason, techniques have been developed which aim to detect signs of fetal hypoxia early enough to allow helpful intervention. In current Western practice, labor and delivery is frequently monitored for signs of fetal distress, especially when the conditions of pregnancy are thought to place the fetus at increased risk. When sufficiently ominous fetal distress signs are observed, rapid induction of labor or surgical delivery by cesarean section are frequently performed in response. Because presently available monitoring devices and methods do not measure fetal oxygen levels directly or do so only intermittently, and/or only at late stages of labor, severe fetal distress sometimes escapes notice. Indirect monitoring techniques also can give misleading indications of fetal oxygen distress (false positives), resulting in surgical intervention that proves to be unnecessary.

The techniques presently employed for fetal monitoring include:
1) Electronic detection and analysis of fetal heartbeat (electrocardiography);
2) Mechanical detection and analysis of fetal heartbeat with stethoscope (auscultation), microphone (phonocardiography), or using ultrasonic waves (ultrasonography);
3) Fetal blood pH measurement by means of an electrode attached to the fetal body; and
4) Fetal blood sampling and analysis (FBS).

All but the last of these techniques do not directly measure fetal oxygen status. Rather, they measure physiological indices which vary in response to fetal hypoxia and other factors. Presently, fetal heartbeat monitoring is the form of fetal monitoring in widest use. Fetal heartbeat monitoring, whether electronic or mechanical, depends upon the observation of a characteristic slowing of the fetal heartbeat (bradycardia) and, in some instruments, alterations in the form of the rhythmic heart signals. Because such alterations in fetal heartbeat can arise from causes other than hypoxia, and because interpretation of the heartbeat signal for evidence of distress can be difficult, this form of monitoring does not provide a completely reliable means of detecting fetal oxygen distress.

A further limitation of fetal heartbeat monitoring is that a clear fetal heartbeat signal is not continuously obtainable from most patients. From 20% to 50% of the time, according to typical reports, no adequate signal is obtainable, and the attending medical personnel are unpredictably left without a reliable indication of fetal condition.

Fetal blood pH tends to decrease (acidity increases) as a result of hypoxia. Fetal pH monitoring, the third technique listed above, is sometimes used in addition to fetal heartbeat monitoring in high-risk pregnancies. However, the use of fetal pH electrodes requires access through the maternal uterine cervix, rupture of the placenta, and the presence of electrical wires connecting the electrode to a measuring device. Further, access is possible only in advanced stages of labor when the cervix is substantially dilated.

Fetal blood sampling, the fourth listed monitoring technique, allows measurements of blood pH and, in principle, of blood oxygen saturation to be made directly. One disadvantage of the method, however, is that isolated individual readings are obtained rather than continuous readings; the technique must be performed repeatedly to avoid false indications for surgery from transient episodes of acidosis or hypoxia that resolve spontaneously. Fetal blood sampling is necessarily invasive, requiring instruments to be inserted through the maternal cervix and small incisions to be made in the fetal scalp (or buttocks, in the case of breech presentations). Complications result from the procedure only infrequently; but the fact that specialized skill and experience in the technique are necessary, along with the limitations described above, have severely limited its clinical use. As with fetal pH monitoring, direct access to the fetus is required, and possible only in late stages of labor.

NMR spectroscopy is described in numerous places including U.S. Pat. No. 4,477,777.

NMR techniques can be used to measure the concentration of various chemical species within the human body, and techniques have been found to elicit signals from specific localized regions within the body. It might, accordingly, be thought that existing NMR methods could be applied to measure the oxygen content of living human fetuses. Such a direct application, however, seems infeasible for reasons including the following:

First, naturally occurring oxygen consists mainly of $^{16}O$, whose nucleus possesses no magnetic moment (hence has gyromagnetic ratio zero) and so cannot be studied by NMR. The natural abundance of $^{17}O$, which does possess a magnetic moment, is only 0.37% and its intrinsic sensitivity is approximately $1.08 \times 10^{-5}$ times that of $^{1}H$. As a result, the NMR signal from oxygen within a natural sample or living creature is only some four billionths as strong as the signal from an equal concentration of hydrogen nuclei within it, effectively ruling out any chance of detection by available methods.

It is known, however, that the binding of oxygen atoms to the oxygen- and carbon dioxide- carrying blood protein hemoglobin so alters the distribution of electrons around the iron atoms within the protein's heme groups, and so alters the conformation of the four amino acid chains that comprise the protein molecule, that a number of proton and carbon resonances are detectably shifted as a result. Consequently, it is feasible to determine the oxygen saturation of hemoglobin by measuring the amplitudes of such resonances and comparing them with the amplitudes of other resonances whose position happens not to be shifted upon oxygen binding (whose chemical shift, that is, is unaffected by normal oxygen binding to the hemoglobin molecule).

The NMR signal from blood within the body of a pregnant human female originates mainly in maternal rather than fetal blood, because the volume of fetal blood comprises no more than 5-10% of the total. Since the oxygenation level of the maternal blood gives little, if any, indication of fetal oxygen levels, means must be found to isolate a signal specifically representative of fetal oxygenation. Existing art offers two methods for distinguishing NMR signals from specified spatial regions: magnetic resonance imaging (MRI) and spatial localization through the use of shaped magnetic fields and/or specialized radio frequency antennas. MRI, whether accomplished by pulse-gradient techniques, focused magnetic fields (FONAR), or otherwise, extracts NMR signals from individual small volume elements such as cubes, or thin two-dimensional sections such as flat planes, and from a succession of these signals, constructs a three-dimensional representation of the object being examined. All such methods are unsuitable for obtaining NMR spectroscopic information from circulating blood for two reasons. First, signal-to-noise ratios decline to impractically small levels for NMR spectroscopy as the effective sampling volume is reduced to the size of volume elements employed in MRI. Second, the relaxation times characteristic of useful resonances in blood are too long: excited nuclei spend considerably less time within an imaging volume element than the characteristic relaxation periods as a result of normal blood circulation. Excited nuclei will therefore have left a volume element before an NMR signal can be obtained from them.

Spatial localization of NMR signals can be accomplished through the use of static-field magnets designed to produce a homogeneous field only within a limited region, and whose field outside the region of interest increases or declines rapidly. As a result, resonance conditions can occur only within the homogeneous region. A form of spatial localization can also be achieved through the use of specially shaped radio frequency transmitting and receiving antennas (or combination transmitting-receiving antennas), such as circular or semi-toroidal surface coils, which transmit and receive signals efficiently only from nearby regions. Such a coil, placed against the surface of a human body, typically conveys NMR signals only from a region within the body of dimensions comparable to those of the coil. The use of shaped magnetic fields and surface coils can be combined for localized NMR spectroscopy. Existing methods, however, provide no means for such localized spectroscopy where the target volume is constantly changing shape and position, as does the fetus within a pregnant woman. Unless the location of the fetus with respect to the NMR apparatus were continuously determined, and the shape of the constant-field region of the static magnetic field somehow adjusted to precisely conform to the fetus, the NMR signals would contain an unknown and constantly varying contribution from maternal tissues and blood.

Because NMR can in principle be used to examine chemical reactions within the interior of the body, non-invasively and with essentially no known hazards, and because present fetal monitoring techniques are inadequate, the motivation remains to discover methods for using NMR to monitor fetal physiology.

SUMMARY OF THE INVENTION

Accordingly, it is the object and purpose of the present invention to provide a method for continuously monitoring fetal oxygen levels, along with other useful physiological variables prior to and during labor and delivery. This method uses the phenomenon of nuclear magnetic resonance, is applicable to human fetuses and newborns as well as to certain other mammals, and is capable of detecting signs of fetal distress that may signal the need for medical intervention. The method can also serve to detect the absence of fetal hemoglobin in fetuses and newborns, such as occurs in pathological hereditary absence of fetal hemoglobin, and can be used to detect the abnormal presence of fetal hemoglobin in children and adults, as in cases of hereditary persistence of fetal hemoglobin.

The present invention makes use of the observation that certain distinctive nuclear magnetic resonances originating in specific atomic nuclei within the human oxygen-carrying protein hemoglobin (Hb) are displaced to a measurable degree as a result of reversible oxygen binding to the iron atoms within the hemoglobin molecule. Other hemoglobin resonances, usually originating in nuclei within amino acids located far from the heme groups of hemoglobin, show no measurable displacement upon oxygen binding. Comparison of the magnitude of the NMR signal corresponding to such an oxygenation-displaced resonance with the magnitude of the NMR signal corresponding to an oxygenation-insensitive resonance gives a quantitative measure of the percentage of hemoglobin molecules carrying oxygen, i.e. the fraction of hemoglobin molecules in one of the oxyhemoglobin states and the complementary fraction of hemoglobin molecules in the deoxyhemoglobin state. The invention makes use of the further observation that a special form of hemoglobin (fetal hemoglobin or HbF) typically constitutes 80% of the hemoglobin in the blood of human fetuses for many months prior to birth, but is present in the maternal blood of normal mothers in concentrations of typically 5% or less. This fetal form of hemoglobin gives rise to one or more oxygenation-displaced resonances and one or more oxygenation-insensitive resonances that are distinguishable from the resonances originating in normal adult-form hemoglobin (HbA). Measuring and comparing the intensities of such a pair of HbF resonances provides a means for determining the percentage of oxygenated and deoxygenated fetal hemoglobin molecules, distinguished from the percentage of oxygenated and deoxygenated adult hemoglobin molecules that may be present in the same sample or spatial volume being analyzed.

The invention will be further described with reference to the accompanying drawings, wherein.

Figure 1:
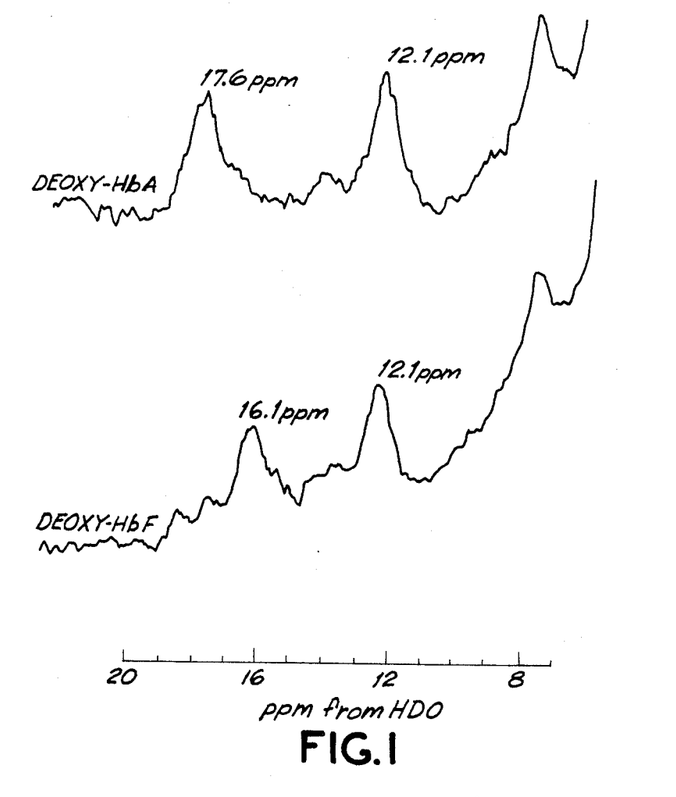
FIG. 1 is a 90 MHz spectra of deoxyhemoglobins A and F in 0.1M deuterated phosphate buffer at 30° C., pD 7.
Figure 2:
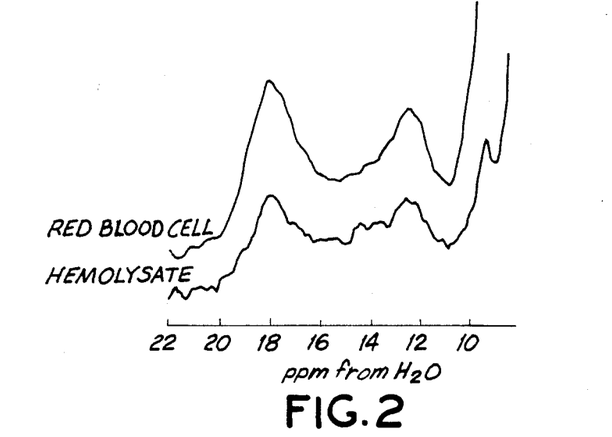
FIG. 2 is a 250 MHz proton NMR spectra of deoxyhemoglobin A inside red blood cells and in hemolysate at 27° C.

Nuclear magnetic resonances characteristic of the deoxygenated state of HbA and HbF include the hyperfine-shifted (hfs) resonances in the proton NMR spectrum between 7 and 22 ppm downfield, and between −12 and −24 ppm upfield from HDO (hydrogen deuterium oxide). Two resonances of particular interest are the contact-shifted resonances that occur at approximately 17.6 ppm and 12.1 ppm downfield from HDO (as measured in 0.1M deuterated phosphate buffer at 30° C., pD=7) in the spectrum of HbA. As can be seen in FIG. 1, the HbF resonance corresponding to the first of these two HbA resonances is shifted upfield to approximately 16.1 ppm, and is readily distinguished from it. Because of their large hyperfine shifts, these resonances are widely separated from the rest of the Hb proton NMR spectrum and can be readily distinguished against a background of other blood protein resonances, as is evident in FIG. 2. And it has been established that the intensity of these two resonances increases in proportion to the amount of deoxy Hb present in a mixture of deoxy Hb and oxygenated hemoglobin molecules (see, for example, FIG. 5 in Ho and Russu, "Proton Nuclear Magnetic Resonance Investigation of Hemoglobins", Methods in Enzymology, 76, pp. 275–312 (Academic Press, NY, 1981)). The intensity of the 16.1 ppm hfs resonance is, therefore, a measure of the quantity of deoxygenated fetal hemoglobin molecules in a mixture, while the intensity of the 17.6 ppm hfs resonance measures the quantity of deoxygenated adult-type hemoglobin molecules.

Nuclear magnetic resonances characteristic of the oxygenated states of HbA and HbF include the ring-current-shifted resonances in the proton NMR spectrum between $-5$ and $-7$ ppm upfield from HDO. Three resonances of interest in the HbF spectrum occur at $-5.55$ ppm, $-5.31$ ppm, and $-6.80$ ppm upfield from HDO in the proton spectrum of HbCO, which closely approximates the spectrum of oxyhemoglobin. These three resonances can be distinguished from the HbA resonances at $-5.86$ ppm, $-5.42$ ppm, and $-6.58$ ppm upfield from HDO, displayed in FIG. 3. These resonances are characteristic of oxygenated hemoglobin (and HbCO) and do not appear in deoxygenated Hb. See, Ho et al., "Nuclear Magnetic Resonance Studies of Hemoglobin IV", Biochemical and Biophysical Research Communications, 38, pp. 779–785 (1970). (The resonances at $-5.86$ ppm and $-6.58$ ppm in HbCOA have been assigned to the $\gamma_1$ and $\gamma_2$ methyls of $\beta$E11 valine. All of the chemical shifts given here are intended to identify particular nuclear magnetic resonances rather than to be precise determinations; signs follow the current (1974) IUPAC convention.) Suitable combinations of nuclear magnetic resonances characteristic of deoxygenated and of oxygenated states of hemoglobin, and specific to fetal and adult forms of the molecule can be selected from these examples.

The invention applies these observations in a novel application of NMR spectroscopy to determine the degree of oxygenation of hemoglobin molecules in the blood and tissues of human fetuses, hence the fetal respiratory oxygen status, and to measure other physiological variables of interest. Because alterations in blood pH slightly displace certain HbF resonances, the method can also be used to monitor fetal blood acidity.

Figure 3:
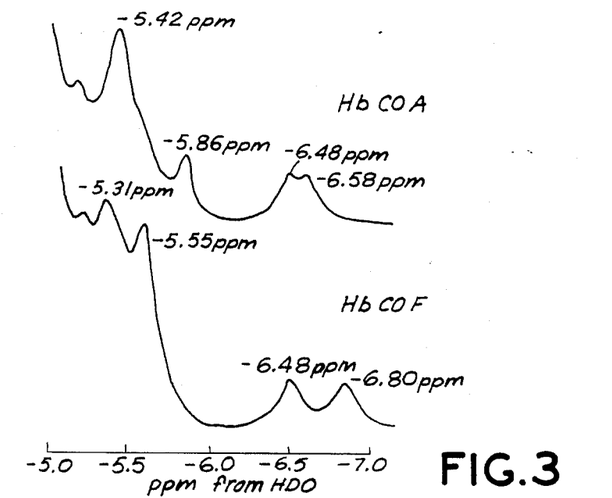
FIG. 3 is a 250 MHz proton NMR spectra of carbonmonoxyhemoglobins A and F in 0.1M deuterated phosphate buffer at 32° C., pD 7.
Figure 4:
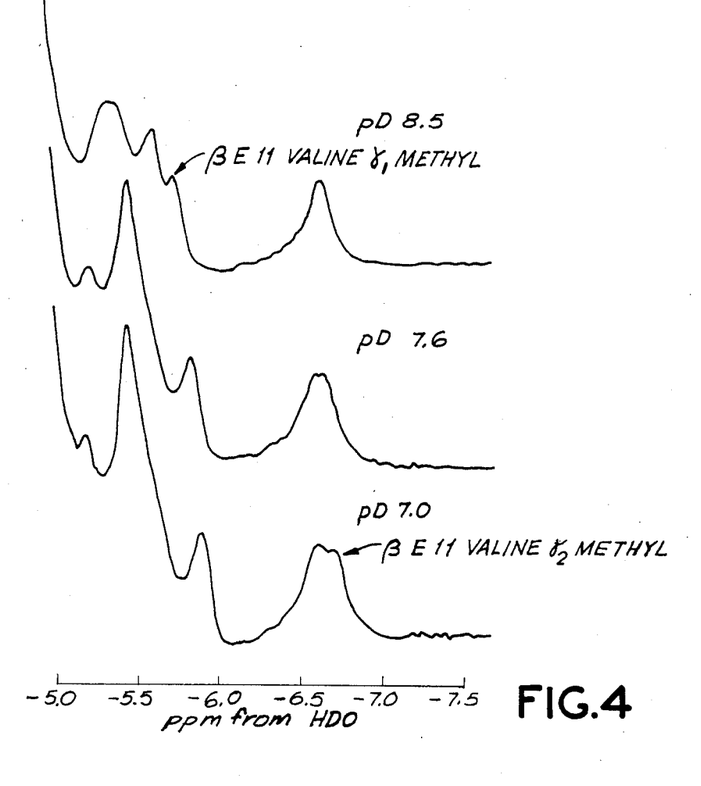
FIG. 4 is a 250 MHz spectra of HbCOA in 0.1M deuterated bistris buffer, 4 mM 2,3-diphosphoglycerate (DPG) at 31° C., at three different pD values.

Surface histidyl residues of hemoglobin are known to give rise to proton NMR signals that are strongly dependent on the pH and ionic constitution of the liquid medium surrounding the protein. Proton NMR spectroscopy has in fact been used to determine intracellular pH levels by measuring such signals to a reported precision of 0.03 pH unit. Other Hb resonances are sensitive to pH changes, as well, including proton resonances specific to HbA and to HbF. Among these pH-sensitive resonances are certain of the ring-current-shifted resonances between $-5.0$ ppm and $-7.0$ ppm upfield from HDO, as can be seen in FIG. 4. As pD is lowered from pD 8.5 to pD 7.0, the chemical shift of the $\beta$E11 valine $\gamma_1$ resonance, identified at $-5.86$ ppm in FIG. 3, decreases by approximately 0.2 ppm. As can be seen in FIG. 3, this resonance is characteristic of HbA; the corresponding resonance in HbF is shifted substantially (on account of amino acid substitutions in the $\beta$ chain of the protein at E14 and E15 in the fetal form). The resonance is therefore suitable for monitoring adult-specific blood pH, and the corresponding HbF resonance is appropriate for monitoring fetal-specific blood pH.

Because each beat of the heart and each respiration momentarily affects the blood oxygenation to a small degree, the fetal oxygenation signal, if sufficiently clear, also can be processed to yield a continuous indication of fetal heart rate and respiration.

Figure 5:
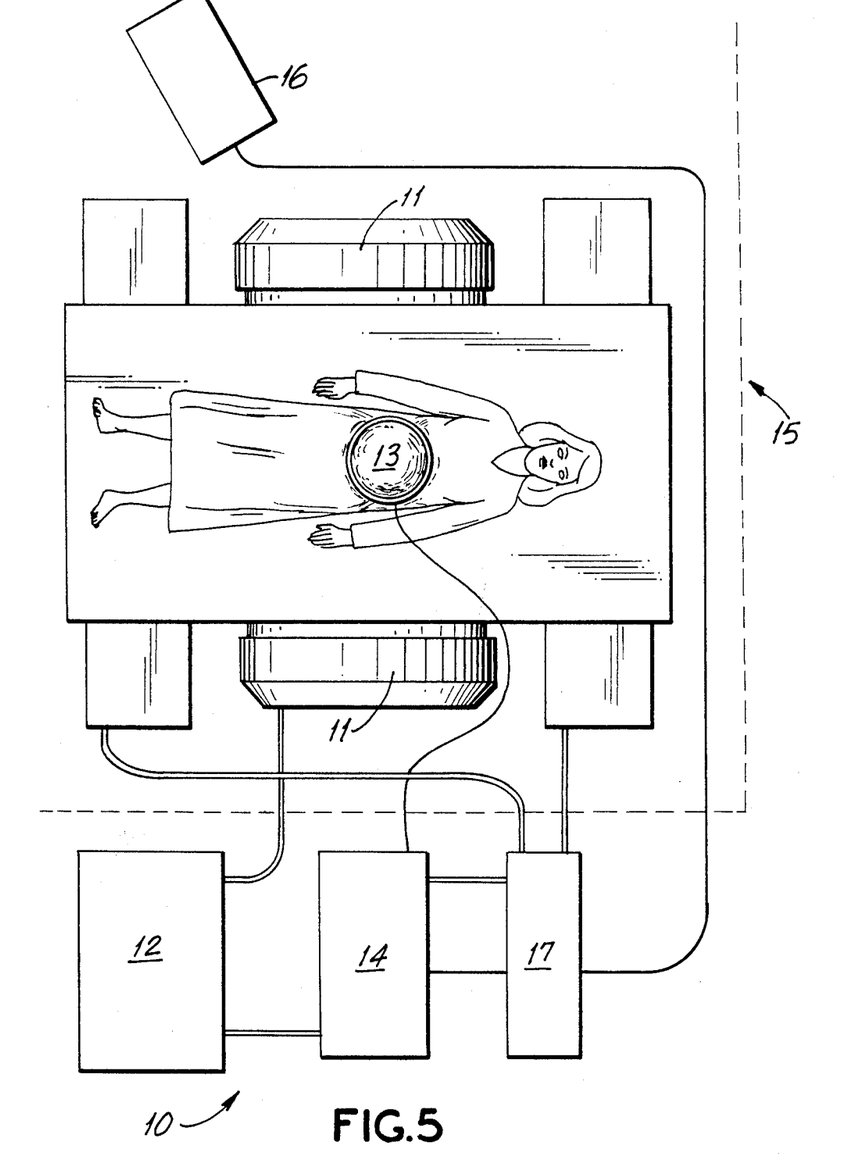
FIG. 5 is a top schematic view of the fetal monitoring apparatus.
Figure 6:
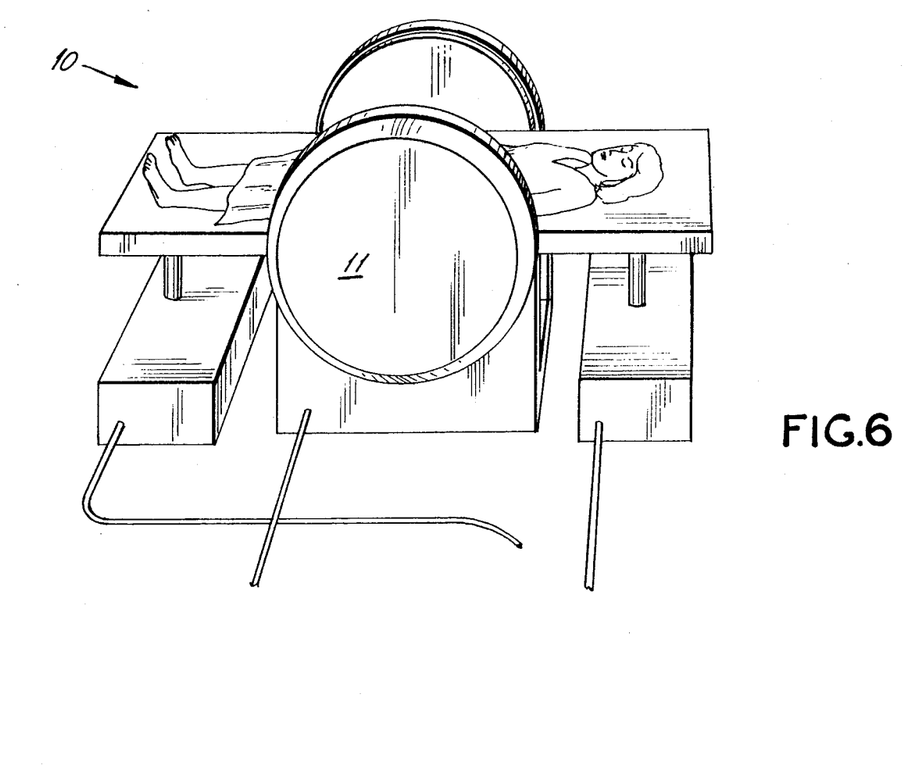
FIG. 6 is a side schematic view of the fetal monitoring apparatus shown in FIG. 5.

To carry out the measurements described in the foregoing, there is provided an apparatus 10 as shown in FIG. 5 and FIG. 6 for determining fetal oxygen levels and related physiological variables consisting of the following:

(1) A magnet 11 capable of producing a static nearly uniform magnetic field of approximately 0.1 to 1 Tesla or more throughout a region of space approximated by a sphere of 30 cm diameter or more, with an air space, bore, or other opening or surface large enough to comfortably admit the abdomen of a pregnant woman at term. The static-field magnet 11 may be of permanent-magnet, superconducting, or conventional electromagnet type. The magnet 11 may be an air-gap design, with opposing pole-pieces enclosing the region of constant field, or of solenoidal design, containing the region of constant field within a cylinder, or of unilateral design, producing an approximately constant magnetic field within a region entirely to one side of a plane bounding the magnet, such as described in U.S. Pat. No. 4,721,914. The magnet 11 is provided with means for centering the constant-field region within the abdomen of a pregnant woman within or next to the magnet 11 as appropriate, either by mechanical means 17 or through the use of accessory shim coils 12 or both, and either under manual control or under the control of automatic servomechanisms which may be part of a feedback control circuit incorporating signals from the NMR spectrometer device described below.

(2) NMR transmitting and receiving antennas 13, or a combined transmitting and receiving antenna 13 appropriate to send and receive radiofrequency electromagnetic radiation selectively to and from a limited region of space comparable in size to a large human fetus at term. Such antenna 13 or antennas may have the form of a simple flat coil, or semi-toroidal coil, insulated and suitable for placement directly upon the abdomen of a pregnant woman (or other pregnant female mammal) or upon the abdomen of an infant. Alternatively, the antenna 13 or antennas may have any other form suitable for collecting NMR signals from the region within the human body occupied by a mature fetus when such antenna or antennas are placed at appropriate locations outside or alongside the maternal body. Further specialized antennas, of surface coil or other design may be provided for the measurement of maternal oxygen saturation and other physiological variables of pregnant mothers, human beings in general, newborn infants, and in animals other than humans.

(3) NMR spectroscopy electronic apparatus 14 capable of producing high resolution spectra either by Fourier pulse analysis, by correlation spectroscopy or in continuous wave operation, consisting of radiofrequency transmitter, receiver, pulse-generator, Fourier analysis, logic and other circuits, and supplemented by signal-processing circuitry which may be under microprocessor control. The circuitry is of appropriate design to perform functions including signal averaging, solvent peak suppression, and such related functions as are known to those skilled in the art of NMR spectroscopy as methods for facilitating the detection and measurement of specific nuclear magnetic resonances. Microprocessor-controlled circuitry is suitable to carry out, among other functions, recognizing specific resonances of interest, computing resonance amplitudes and chemical shifts, and from these continuously calculating values of fetal oxygen saturation, blood pH, pulse rate, and respiration rate. Further, provision can be made to detect and measure corresponding resonances of HbA and to compute from these measurements the level of oxygenation of the maternal blood as well as the maternal heart rate, respiration rate and blood pH. Circuitry may also provide control signals to shim-magnet-controlling and magnet-positioning servomechanisms mentioned above.

(4) Magnetic and electromagnetic shielding 15 to surround the system, as appropriate to prevent interference from nearby sources of magnetic and electromagnetic fields and to limit magnetic and electromagnetic leakage from the system.

(5) A bedside display console 16 providing an easily readable display of calculated fetal oxygen levels, pulse rate, respiration rate, blood pH level, and other physiological variables of interest, along with alarm lights and audible signals suitable for providing a warning of potentially dangerous fetal or maternal conditions.

Application of the method proceeds according to the following steps:

(1) Positioning of the subject within the field of the static-field magnet and operation of mechanical positioning devices and magnet shim coils as necessary to center the region of approximately constant magnetic field on the fetus.

(2) Operation of the NMR spectrometer to identify and measure the amplitude of two or more NMR signals originating in fetal hemoglobin (HbF) molecules, including at least one of the following combinations:
  (a) One resonance characteristic of deoxygenated Hb and one resonance characteristic of oxygenated Hb;
  (b) One resonance characteristic of oxygenated Hb and one resonance present in both oxygenated and deoxygenated Hb;
  (c) One resonance characteristic of deoxygenated Hb and one resonance present in both oxygenated and deoxygenated Hb.

(3) Feedback of spectrometer signals to positioning and shimming control devices, if desired.

(4) Computation of the fraction of fetal hemoglobin molecules in an oxygenated state, based on comparison of the measured NMR signal amplitudes, corrected for nonzero baseline, overlapping resonance signals, such as solvent resonances, and for known instrument nonlinearities, as follows:

(a) $f_O = \dfrac{A_O}{A_O + A_D}$ (b) $f_O = A_O/A$ (c) $f_O = 1 - A_D/A$ where $A_O$ is the amplitude of an NMR signal characteristic of oxygenated Hb, $A_D$ is the amplitude of an NMR signal characteristic of deoxygenated Hb, $A$ is the amplitude of a signal characteristic of Hb, independent of its oxygenation state, and $f_O$ is the fraction of Hb molecules in an oxygenated state.

(5) Computation of the degree of oxygen saturation of fetal blood and tissues, either by adjusting the fractional oxygenation values to account for the quantity of oxygen carried by hemoglobin molecules in the four possible oxygenation states (with one, two, three, or four bound oxygens) or by reference to the empirical relationship between fractional hemoglobin oxygenation and measured blood oxygen saturation. Computation may be adjusted to account for the small percentage of HbF present in maternal blood.

(6) If readings of maternal oxygen saturation levels are desired, the above procedure is repeated, substituting HbA-specific NMR signals for fetal-specific ones.

(7) Operation of NMR spectrometer to identify and precisely determine the chemical shift of NMR signals originating in fetal or in adult-type hemoglobin molecules, whose chemical shift is known to vary significantly with changes in solvent pH; and computation of fetal or maternal blood pH, respectively, by reference to the empirical relationship between chemical shift displacement and measured blood pH.

(8) Operation of the NMR spectrometer to detect small, rhythmic variations in oxygenation-sensitive Hb resonance amplitudes resulting from respiration and the operation of the heart; calculation of fetal respiratory rate and heart rate or maternal respiratory rate and heart rate, according to the origin of the NMR signals in HbF or HbA.

(9) Transmission of readings obtained in the preceding steps to a bedside display console for display, recording, and the operation of appropriate alarms when preset tolerances are exceeded.

It will be seen from the foregoing that the invention utilizes the idea, novel in the fields of blood gas measurement, oximetry, and fetal monitoring, of determining the oxygen saturation of blood using nuclear magnetic resonance, in particular to analyze the oxygenation state of hemoglobin proteins in the blood. In order to distinguish fetal blood oxygenation from maternal blood oxygenation within a pregnant human female, the state of fetal-type hemoglobin molecules is analyzed. The invention also uses a combination of shaped magnetic fields (that is, a static magnetic field homogeneous over a limited region of interest, but varying substantially from the homogeneous-field value outside the region) and specialized transmitting and receiving coils, such as surface coils, to delimit the region subjected to NMR analysis to a region approximating that occupied by the fetus. The invention combines this form of approximate spatial localization with the novel form of oxygenation analysis described above which specifically distinguishes NMR signals from fetal blood from signals originating in maternal blood, in order to achieve further discrimination between signals originating in the fetal volume and signals originating in the maternal blood and tissues.

PREFERRED EMBODIMENT OF THE INVENTION

A preferred embodiment of the invention consists of NMR spectroscopy apparatus, as described above, and meeting the following specifications:

An air-gap magnet capable of producing a magnetic field of approximately 0.1 to 1.0 Tesla or more, nearly homogeneous over a central region roughly approximated by a 30 cm diameter sphere;

A transmitting and receiving antenna of approximately circular shape (a conventional NMR surface coil) and approximately 25 cm diameter, suitable for obtaining NMR signals from a volume within a pregnant woman comparable to the volume of a large normal fetus at term, at a depth within the mother (as measured from the surface of the abdomen to the approximate geometrical center of the fetus) of approximately 10–25 cm, and suitable for placement directly upon the maternal abdomen.

NMR spectroscopy apparatus as described above and specifically designed to detect, identify, and measure the proton resonance associated with adult human hemoglobin in the deoxy state at approximately +17.6 ppm (parts per million downfield from HDO; sign according to IUPAC convention, chemical shifts measured at 30° C. in 0.1M deuterated phosphate buffer at pD 7), as well as the resonances associated with human fetal hemoglobin at approximately +16.1 ppm and 12.4 ppm. The apparatus is further designed to detect, identify, and measure the resonances associated with adult human hemoglobin, normal oxygenated form, at approximately −5.42 ppm, −5.86 ppm, and −6.58 ppm upfield from HDO, as well as the corresponding resonances associated with fetal hemoglobin at approximately −5.31 ppm, −5.55 ppm and −6.80 ppm. The resonances at −5.86 ppm and −6.58 ppm in adult oxyhemoglobin are believed to originate in the $\gamma_1$ and $\gamma_2$ methyls of the 67E11 valines in the beta chains of HbA.

It will be understood that the specification and examples are illustrative but not limitative of the present invention and that other embodiments within the spirit and scope of the invention will suggest themselves to those skilled in the art.

We claim:

1. A method of determining the oxygenation level of an animal which comprises:
    (a) obtaining an NMR spectrum originating in the hemoglobin molecules of the animal;
    (b) determining the amplitude of a nuclear magnetic resonance (NMR) signal from said NMR spectrum which originates in a nucleus within the hemoglobin molecules of the animal and which has a chemical shift characteristic of the hemoglobin oxygenation level;
    (c) determining the amplitude of an NMR signal from said NMR spectrum which originates in a nucleus within the hemoglobin molecules of the animal and which has a chemical shift independent of the hemoglobin molecule oxygenation level; and
    (d) determining a ratio of the first determined amplitude from step (b), to the second determined amplitude from step (c), the ratio constituting a measure of the oxygenation level of the animal.

2. The method according to claim 1, wherein the animal is a living fetus within its mother.

3. A method of determining the oxygenation level of a living fetus within its mother which comprises:
    (a) obtaining an NMR spectrum originating in the total hemoglobin of the mother and fetus;
    (b) determining the amplitude of a first fetal nuclear magnetic resonance (NMR) signal from said NMR spectrum which originates in a nucleus within the fetal hemoglobin (HbF) molecules of the fetus, which is characteristic of fetal hemoglobin (HbF) molecules and distinguishable from nuclear magnetic resonance signals originating within the adult-type hemoglobin (HbA) molecules of the mother, and which has a chemical shift characteristic of the fetal hemoglobin oxygenation level;
    (c) determining the amplitude of a second fetal NMR signal which originates in a nucleus within the fetal hemoglobin (HbF) molecules of the fetus, which is characteristic of fetal hemoglobin (HbF) molecules and distinguishable from nuclear magnetic resonance signals originating within the adult-type hemoglobin (HbA) molecules of the mother, and has a characteristic chemical shift independent of the fetal hemoglobin oxygenation level; and
    (d) determining a ratio of the first determined amplitude from step (b), to the second determined amplitude from step (c), the ratio constituting a measure of the oxygenation level of the fetus.

4. The method according to claim 3, wherein NMR analysis is performed on a volume of space approximating the region of space occupied by the fetus in the mother through the use of NMR transmitting and receiving means designed to transmit and receive NMR signals to and from the volume of space.

5. The method according to claim 3, wherein further analysis of the NMR signals is performed in order to measure pH-dependent shifts in hemoglobin NMR signals so as to obtain an indication of changes in blood acidity of the fetus or the mother.

6. The method according to claim 5, wherein the pH-dependent shifts in hemoglobin NMR signals are the ring-current-shifted proton resonances found between approximately −5.0 and −7.0 ppm upfield from HDO in HbCO.

7. The method according to claim 5, wherein further analysis of the NMR signals is performed in order to detect small periodic variations in blood oxygenation that result from rhythmic activity of the heart and lungs of the fetus or the mother, so as to obtain an indication of fetal heartbeat, fetal respiration, maternal heartbeat, maternal respiration or any combination thereof.

8. The method according to claim 5, wherein NMR analysis is performed on a volume of space approximating the region of space occupied by the fetus in the mother through the use of shaped magnets designed to produce a constant substantially uniform magnetic field throughout the volume of space.

* * * * *